US011280784B2

(12) United States Patent
Sagle (10) Patent No.: US 11,280,784 B2
(45) Date of Patent: Mar. 22, 2022

(54) PATTERNED PLASMONIC NANOPARTICLE ARRAYS FOR MULTIPLEXED, MICROFLUIDIC BIOSENSING ASSAYS (71) Applicant: University of Cincinnati, Cincinnati, OH (US)

(72) Inventor: Laura Sagle, Cincinnati, OH (US)

(73) Assignee: University of Cincinnati, Cincinnati, OH (US)

(*) Notice: Subject to any disclaimer, the term of this patent is extended or adjusted under 35 U.S.C. 154(b) by 897 days.

(21) Appl. No.: 15/932,300

(22) PCT Filed: Aug. 19, 2016

(86) PCT No.: PCT/US2016/047686
§ 371 (c)(1),
(2) Date: Feb. 16, 2018

(87) PCT Pub. No.: WO2017/031393
PCT Pub. Date: Feb. 23, 2017

(65) Prior Publication Data
US 2020/0284788 A1   Sep. 10, 2020

Related U.S. Application Data (60) Provisional application No. 62/206,897, filed on Aug. 19, 2015.

(51) Int. Cl.
*G01N 33/543* (2006.01)
*G01N 33/487* (2006.01)

(52) U.S. Cl.
CPC . *G01N 33/54373* (2013.01); *G01N 33/48707* (2013.01); *G01N 33/54346* (2013.01)

(58) Field of Classification Search
CPC ....... G01N 33/48707; G01N 33/54346; G01N 33/54373; G03F 7/40
USPC ........................................ 436/524
See application file for complete search history.

(56) References Cited

U.S. PATENT DOCUMENTS

| | | |
|---|---|---|
| 2005/0224779 A1 | 10/2005 | Wang et al. |
| 2010/0080954 A1 | 4/2010 | Mohseni |
| 2010/0210008 A1 | 8/2010 | Strand et al. |
| 2010/0291697 A1* | 11/2010 | Mirkin ............. C01G 5/00 436/94 |
| 2011/0048947 A1 | 3/2011 | Petronis et al. |
| 2011/0177460 A1* | 7/2011 | Shi ............. C23C 14/0641 430/324 |
| 2011/0261364 A1 | 10/2011 | Nieva et al. |
| 2012/0188551 A1 | 7/2012 | Langhammar et al. |
| 2013/0149492 A1* | 6/2013 | Yoon ............. B29C 67/20 428/137 |
| 2014/0336084 A1 | 11/2014 | Pugia et al. |
| 2015/0253321 A1* | 9/2015 | Chou ............. G01N 33/54386 435/5 |

OTHER PUBLICATIONS

Fredriksson (2007) Adv Mat 19:4297-4302 (Year: 2007).*
International Search Report & Written Opinion for corresponding PCT/US2016/047686 dated Nov. 10, 2016.
Dixit, Chandra and Kaushik, Ajeet, "Nano-strucdtured arrays for multiplex analyses and Lab-on-a-Chip applications," Biochemical and Biophysical Research Communications 419 (2012) 316-320.

* cited by examiner

*Primary Examiner* — Ann Montgomery
(74) *Attorney, Agent, or Firm* — Dinsmore & Shohl LLP (57) ABSTRACT

Methods for fabricating a localized surface plasmon renosance (LSPR) biosensing microfluidic or spot-plate device that combines the techniques photolithography and hole-mask colloidal lithography in a unique way to yield highly sensitive yet cost-efficient devices capable of miniaturization and portability, along with the devices and methods of utilizing the devices are disclosed. The desired device pattern is transferred to a photoresist on a substrate using photolithography; at least two coats of polymer are spin-coated onto the substrate to form a polymer layer, a plurality of polystyrene particles of a desired shape and size are drop-coated on the polymer layer, a nanomeric layer of gold is deposited thereover, the polystyrene particles are removed, the hole-mask is etched, a plasmonic metal is deposited into the holes, and the polymer layer and photoresist are then removed prior to optionally sealing with a cover.

22 Claims, 8 Drawing Sheets

PATTERNED PLASMONIC NANOPARTICLE ARRAYS FOR MULTIPLEXED, MICROFLUIDIC BIOSENSING ASSAYS

PRIORITY CLAIM

This application claims priority under 35 U.S.C. § 119 to U.S. provisional application Ser. No. 62/206,897 filed on Aug. 19, 2015, the entire disclosure of which is incorporated herein by this reference.

TECHNICAL FIELD

The subject matter of this application relates to methods for fabricating highly sensitive Localized Surface Plasmon Resonance (LSPR)-based biosensors that are capable of miniaturization for microchip applications and which produce a signal salient enough to be read by cost-efficient standard detection methodology, thus rendering the biosensors fully portable and suitable for point-of-care and low-resource contexts.

BACKGROUND

Current point-of-care diagnostics often require the testing of several biomarkers simultaneously, in order to reduce the risk of false diagnosis. (See, e.g. Zethelius, B. et al. *New Engl J Med* 2008, 358, 2107-2116, Gowda, G. *Expert Rev Mol Diagn* 2008, 8, 617-633.) Multiplexed and microfluidic devices provide platforms with which to do these assays, often reducing sample drift, reaction time and minimizing sample volume. In order to extend these technologies to resource limited environments, additional requirements must be met, such as simple, fast readout in addition to a robust, inexpensive and portable platform. (Tokel, O. et al. Advances in Plasmonic Technologies for Point of Care Applications. *Chem Rev* 2014, 114, 5728-5752, the entire disclosure of which is incorporated herein by this citation.) Many of the currently used multiplexed platforms, such as fluorescence and electrochemical assays, are prohibitively expensive and too fragile for use in the field.

Localized surface plasmon resonance (LSPR) biosensing offers label-free, sensitive, colorimetric detection at a relatively low cost (see Sagle, L. B et al. Advances in localized surface plasmon resonance spectroscopy biosensing. *Nanomedicine-Uk* 2011, 6, 1447-1462, and Mayer, K. M. et al. Localized Surface Plasmon Resonance Sensors. *Chem Rev* 2011, 111, 3828-3857, the entire disclosures of which are incorporated herein by this citation). With sensitivities comparable to surface plasmon resonance (SPR) and quartz crystal microbalance (QCM), LSPR offers colored, transparent substrates which can be measured using simple instrumentation or even by eye. Moreover, this nanoparticle-based technology is particularly amenable to miniaturized devices since the sensing elements themselves are small. It is therefore ideal to combine LSPR biosensing with miniaturized on-chip devices for portable point-of-care diagnostics.

Towards this goal, recent studies have combined SPR and LSPR-based sensors into miniaturized, on-chip devices. Highly multiplexed spot plates composed of planar gold and core-shell gold structures have been fabricated and successfully applied towards DNA hybridization and biomarker characterization (Campbell, K. et al. Use of a novel microfluidic device to create arrays for multiplex analysis of large and small molecular weight compounds by surface plasmon resonance. *Biosens Bioelectron* 2011, 26, 3029-3036, and Endo, T. et al. Multiple label-free detection of antigen-antibody reaction using localized surface plasmon resonance-based core-shell structured nanoparticle layer nanochip. *Anal Chem* 2006, 78, 6465-6475, the entire disclosures of which are incorporated herein by this citation). ENREF 6 Moreover, several recent reports have utilized multiplexed and microfluidic gold and silver nanohole arrays, which are sensitive, transparent substrates capable of amplified detection particularly when substrates are flowed through the nanoholes (Barik, A. et al. Dielectrophoresis-Enhanced Plasmonic Sensing with Gold Nanohole Arrays. *Nano Lett* 2014, 14, 2006-2012, Cetin, A. E. et al. Handheld high-throughput plasmonic biosensor using computational on-chip imaging. *Light-Sci Appl* 2014, the entire disclosures of which are incorporated herein by this citation). In addition, encasing the nanohole arrays in silica not only allows interfacing of LSPR substrates with supported lipid bilayers, but also enables facile microfluidic device fabrication (Lee, S. H. et al. Real-time full-spectral imaging and affinity measurements from 50 microfluidic channels using nanohole surface plasmon resonance. *Lab Chip* 2012, 12, 3882-3890, the entire disclosure of which is incorporated herein by this reference). Lastly, an unprecedented degree of multiplexing has been created using single nanoparticles of different shapes immobilized in microfluidic channels or spots of nanoparticle arrays, made using e-beam lithography, within microfluidic channels (Ahijado-Guzman, R. et al. Plasmonic Nanosensors for Simultaneous Quantification of Multiple Protein-Protein Binding Affinities. *Nano Lett* 2014, 14, 5528-5532, and Acimovic, S. S. et al. "LSPR Chip for Parallel, Rapid, and Sensitive Detection of Cancer Markers in Serum" *Nano Lett* 2014, 14, 2636-2641, the entire disclosures of which are incorporated herein by this reference). ENREF 11

However, despite all the apparent advantages of LSPR biosensors, several drawbacks exist with respect to the current state of the art in this technology that limits access and utility to well-funded and well-equipped centralized locations. Detection of molecular binding events of the substrates noted above typically involves confocal microscopy and projection onto a CCD camera, which is not commonly accessible in many research laboratories, and even less so on the field. There remains a need in the art for fast, scalable cost-efficient manufacture of LSPR biosensor-based diagnostic protocols and platforms that are relatively inexpensive, scalable, and which avoid dependence on complex, expensive detection schemes.

SUMMARY

Accordingly, the present inventors developed a novel fabrication method that combines Hole Mask Colloidal Lithography (Fredriksson, H. et al. Hole-mask colloidal lithography. *Adv Mater* 2007, 19, 4297) with photolithography to pattern nanoparticle arrays onto a substrate. This procedure allows for facile, scalable, inexpensive fabrication combined with high sensitivity such that detection that can be achieved with the naked eye, various I-phone apps and with a standard Ultraviolet-Visual spectrometer or plate readers common to most research laboratories. Hole mask colloidal lithography offers an inexpensive, scalable means to pattern dense, uniform nanoparticle arrays in which the size and sensitivity of the nanoparticles can be easily tuned.

Broad embodiments provide methods for fabricating a localized surface plasmon renosance (LSPR) biosensing devices comprising a plurality of plasmonic nanoparticle arrays, the methods comprising: patterning device channels and/or wells onto a substrate with photolithography; and patterning uniform nanoparticle arrays onto the substrate with hole-mask colloidal lithography.

According one embodiment, the method comprises (a) transferring a desired pattern to a photoresist on a substrate using photolithography; (b) spin coating a poly(methylmethacrylate) (PMMA) over the patterned photoresist and spin coating poly(diallyldimethylammonium chloride) (PDDA) over the PMMA to create a polymer layer; (c) drop coating a plurality of polystyrene particles of a desired shape and size on the polymer layer; (d) depositing a nanomeric layer of gold; (e) removing the polystyrene particles to create a hole-mask; (f) etching the hole mask to generate a plurality of holes; (g) depositing a metal into the holes; and (h) removing the polymer layer and the photoresist to yield a plurality of nanoparticle arrays in a desired pattern. LSPR biosensing microfluidic devices and/or LSPR biosensing well plates fabricated according to embodiments of the inventive methods area also described.

According to another embodiment, LSPR biosensor-based assays suitable for simultaneously assaying two or more samples for a target analyte are described. In some embodiments the assay comprises providing an embodiment of an inventive LSPR biosensing microfluidic channel device, functionalizing the nanoparticle arrays with a binding partner for the target analyte, adding a sample of interest to the channels, and detecting a change in LSPR signal, wherein detecting is effectuated by an ultraviolet to visual spectrometer. Additional embodiments describe LSPR biosensor-based assays suitable for simultaneously assaying a sample for two or more target analytes, comprising providing an embodiment of an inventive LSPR biosensing spot plate, functionalizing at least one nanoparticle array with a binding partner for each target analyte in the sample, adding an aliquot of sample to each well, detecting a change in LSPR signal, wherein detecting is effectuated by a standard plate reader.

These and other embodiments are expounded and clarified by reference to the Figures and Detailed Description set forth below. Specific embodiments are described herein for purposes of illustration and should not be construed as limiting the scope of the invention, which is defined by the claims appended hereto. The entire disclosures of all references expressly cited are incorporated herein.

BRIEF DESCRIPTION OF THE FIGURES

FIG. 6A. Photograph of a miniaturized spot plate on glass having spot sizes as small as 10 microns. 6B) Photograph of a 12 channel device on a flexible plastic substrate (cellulose acetate).

DETAILED DESCRIPTION

Embodiments of the present invention provide novel methods for scalable, cost-effective production of highly sensitive localized surface plasmon resonance biosensors, specifically microfluidic devices and spot plates comprising precisely patterned nanoparticle arrays. The methods combine photolithography with hole-mask colloidal lithography in a particular production scheme.

Conventional localized plasmon resonance biosensors include a plurality of metal particles arranged on a substrate in a defined pattern. When light is radiated to these metal particles, it causes a resonant vibration of free electrons in the metal particles with a vibrating frequency of electric field of the light, and plasmon excitation occurs around the surfaces of the metal particles. The condition of localized plasmon resonance in this state is determined by the size of the metal particles and a dielectric constant around the particles. In a resonant frequency of the localized plasmon resonance, there emerges a peak of light absorption. In diagnostic applications, the metal particles may be functionalized with a binding partner of a target analyte/biomarker. Upon coupling, a dielectric constant of the surfaces of the metal particles changes, hence changing the condition of the localized plasmon resonance. Accordingly, an interaction of the target analyte with an antigen probe can be sensed by detecting a change of an optical response of the metal particles. The optical response includes absorption, scattering, fluorescence, Raman scattering, and harmonic luminescence.

A "binding partner", as used herein, is a biochemical species capable of forming a specific, typically high-affinity bond with a target analyte. The analyte/binding partner interaction forms a conjugate pair. Not limiting examples include antigen/antibody, hormone/receptor, drug/receptor, effector/receptor, enzyme/substrate, lipid/lipid binding agent, and complementary nucleic acids strands conjugate pairs. Binding partners may be attached to a plasmon-resonance particle by covalent bonding or other molecular forces, e.g., electrostatic or dispersion forces. The binding interaction is typically mediated by an affinity region of the binding partner. Binding partners specifically bind a target analyte with a dissociation constant (KD) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to as low as $10^{-16}$ M) without significantly binding to other molecules. In accordance with embodiments of the invention, the particle is said to be "functionalized" upon attachment of the binding partner.

The term "sample" as used herein relates to a material or mixture of materials containing one or more analytes of interest referred to as target analytes. In particular embodiments, the sample may be obtained from a biological sample such as cells, tissues, bodily fluids, and stool. Bodily fluids of interest include but are not limited to, amniotic fluid, aqueous humor, vitreous humor, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the assay. For example, prior to analysis, the protein/nucleic acid may be extracted from a tissue sample, methods for which are known. In particular embodiments, the sample may be a clinical sample, e.g., a sample collected from a patient. Samples may also consist of an "experimental" sample, i.e., a sample of interest, and a "control" sample to which the experimental sample may be compared.

The term "assaying" refers to testing a sample to detect the presence and/or amount of an analyte. As used herein, the terms "determining," "measuring," and "assessing," and "assaying" are used interchangeably and include both quantitative and qualitative determinations. The word "detecting" means detecting whether something is present or not, as well as quantitatively measuring the amount of something to provide an absolute or relative value, e.g., a value relative to a control analyte.

The words "a" and "an" mean one or a plurality (i.e., "at least one") unless otherwise indicated, e.g., by using the word "single".

One embodiment of the invention is directed to a method for fabricating a localized surface plasmon renosance (LSPR) biosensing device comprising a plurality of nanoparticle arrays. The method comprises: transferring a desired pattern to a photoresist on a substrate using photolithography; spin coating at least two coats of polymer to form a polymer layer; drop coating a plurality of polystyrene particles of a desired shape and size on the polymer layer; depositing a nanomeric layer of gold; removing the polystyrene particles to create a hole-mask, for example by tape stripping with an adhesive tape; etching the hole mask to generate a plurality of holes; depositing a metal into the holes; and (h) removing the polymer layer and the photoresist to yield a plurality of nanoparticle arrays in a desired pattern. In specific embodiments, suitable plastics/polymers for comprising the polymer layer include e.g., cyclic olefin copolymer (COC), poly(methyl methacrylate) (PMMA), polycarbonate (PC), cyclic olefin polymer (COP), liquid crystalline polymer (LCP), polyimide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA) and polydimethylsiloxane (PDMS). According to a specific embodiment, the method comprises spin-coating a polyacrylate, followed by spin-coating poly(diallyldimethylammonium chloride) (PDDA) over the polyacrylate. In very specific embodiments the polyacrylate comprises poly(methylmethacrylate) (PMMA).

In some specific embodiments the LSPR biosensing device is a microfluidic device and the desired pattern comprises microfluidic channels. A poly(dimethylsiloxane) (PDMS) layer comprising a corresponding microfluidic channel pattern is aligned with the substrate. The PDMS layer is then sealed to the substrate in regions that do not contain the nanoparticular arrays. According to other embodiments, the LSPR biosensing device is a spot plate and the desired pattern comprises a spot plate array. A poly(dimethylsiloxane) (PDMS) layer comprising a corresponding spot plate array pattern is aligned the substrate and sealing to the substrate in regions that do not contain the nanoparticle arrays. This prevents between-well sample contamination.

The substrate may be formed from any suitable material including, for example, glass, plastic, flexible plastic and paper. According to specific embodiments, the substrate is glass. Any suitable glass may be used but a preferred substrate has at least a silicon dioxide surface layer. In other specific embodiments the substrate is a flexible plastic. In very specific embodiments, the flexible plastic comprises nitrocellulose acetate. In even more specific embodiments the flexible plastic substrate comprises a flexible plastic strip. The use of flexible plastic substrates permits greater portability, and also renders the devices more adaptable for interfacing with other devices, for example wrapping around optical fibers and optical cables for increased sensitivity. In other very specific applications the flexible plastic substrate platform provides a highly sensitive, portable point-of-care device for assay/diagnosis/screening of patients in regions of limited resources or accessibility or under urgent time frames.

In certain embodiments the nanomeric gold layer is between 1 nm and 10 nm thick, and in very specific embodiments the nanomeric gold layer is 5 nm thick.

The polystyrene spheres may be of the same diameter or different diameters, or size may be distributed in accordance with the needs of an assay. In very specific embodiments the polystyrene particles comprise polystyrene spheres of the same diameter, with the diameter between 1 nm and 40 nm. It is known and predictable that the resonantly scattered wavelength of a spherical particle will increase, or be "red-shifted", with increasing particle diameter and with increasing dielectric constant of the surrounding material. For spherical particles, dipole resonance produces a scattered frequency spectrum having a single peak at a wavelength which is dependent on the material the particle is made from the size of the particle, the shape of the particle, the morphology of the particle, and the local environment. Larger particles have a longer dipole scattering peak wavelength, and smaller particles have a shorter dipole scattering peak wavelength. The spectrum of scattered light may also contain contributions from a particle's quadrupole resonance. For a given shape, a resonant particle scatters predominantly in a particular wavelength band depending on the composition and size of the particle.

The conductive portion responsible for the plasmons can take many different forms, including solid geometric shapes such as spheres, triangular parallelpipeds, ellipsoids, tetrahedrons, and the like, or may comprise spherical, cylindrical, or other shape shells. A dielectric sphere of similar dimensions, having a suitable metal on its surface exhibits plasmon resonances, assuming the shell has a thickness of at least about 3 nm, preferably 5 nm or more of the metal. The metal may be gold, silver, platinum, palladium, lead, iron, titanium, nickel, copper, aluminum, alloy thereof, or combinations thereof, although other materials may be used, as long as the materials' plasma frequency is higher than that of the light signal and the light that is used to generate the light signal. In specific embodiments the metal is silver or gold, and in very specific embodiments the metal is gold. In certain embodiments, where silver is selected, the silver is coated with functionalized silica.

The nanoparticle array may be fabricated for miniaturized applications, for example on a chip. In specific embodiments the array is circular and has a diameter of between about 20 nm and about 400 nm or a non-circular area of between about 320 $nm^2$ and about 12600 $nm^2$.

According to some embodiments, LSPR biosensor-based assays suitable for simultaneously assaying two or more samples for a target analyte are provided. A target analyte may be an analyte of interest in a sample. A microfluidic device embodiment of the invention is fabricated. The channels of the microfluidic device comprise liquid test samples and test reagents (such as detection proteins, detection nucleic acids, light labels, solvents, blocking solutions, etc). The microfluidic device can have multiple fluidic channels. Each of the fluidic channels can have zero, one, or more than one nanoarrays. Fluidic channels may be oriented in different directions depending on the need of the assay. Basic functions such as transportation, mixing, or separation of a fluid in a quantity desired by a user, are typically performed by using a valve or a pump system. To operate the valve or pump system of a microfluidic device, thermal, magnetic, electrical, or pneumatic methods may be used. The surfaces of the nanoparticles of the nanoparticle arrays are functionalized, for example with a binding partner for the target analyte. The sample containing, or thought to contain, the target analyte is added to one or more of the channels and subject to radiation/light. A change in LSPR when compared to a control sample is measured. The microfluidic devices manufactured according to embodiments of the inventive methods provide sufficiently salient signal to be detected by a simple ultraviolet to visual spectrometer. In very specific embodiments, the target analyte is a protein and the binding partner comprises an antibody, or the target analyte is a nucleic acid or polynucleotide and the binding partner comprises a nucleic acid probe.

Another embodiment of a microfluidic device provides a platform for measurement of kinetics of multiple analytes. According to specific embodiments the analytes become kinetically bound by flowing solution through small channels simultaneously.

According to other embodiments, LSPR biosensor-based assays suitable for simultaneously assaying a sample for two or more target analytes are provided. The spot or well-plate is also sometimes referred to as a microwell plate or microplate and is manufactured according to an embodiment of the instant inventions. A microwell plate typically has 6, 24, 96, 384 or 1536 sample wells. Nanoparticle arrays in the wells are functionalized with a binding partner for each target analyte in the sample, and an aliquot of sample is added to each well. A person of ordinary skill in the art understands that the well plate may be partitioned into different sample areas or different reagent areas or whatever meets assay needs. Control wells and the like may be included. The micro well may be read by a standard plate reader. A change in LSPR signal is detected. According to specific embodiments, target analytes are selected from proteins and polynucleotides/nucleic acids and the respective binding partners are selected from antibody and nucleic acid probes.

Other embodiments provide diagnostic methods utilizing LSPR biosensing devices fabricated in accordance with embodiments of the invention. Diagnostic methods may be used for detecting the presence of, or information about, a target analyte or an analyte having a target molecular feature of interest. The target analyte is contacted with at least two or more plasmon resonant particles having surface-functionalized binding partners to the target analyte to produce a particle/target-analyte complex, wherein the target contains a binding partner. The target analyte and binding partner form a conjugate pair selected from the group of pairs consisting of antigen/antibody, hormone/receptor, drug/receptor, effector/receptor, enzyme/substrate, lipid/lipid binding agent and complementary nucleic acid strands. The conjugate pairs are illuminated with an optical light source; and presence of or information about the target is determined by detecting a plasmon resonance spectral emission characteristic of the complex. In very specific embodiments the plasmon resonant particles comprise surface-localized fluorescent reporter molecules, and the interaction of at least two or more plasmon resonant particles with the target analyte is effective to detectably alter a plasmon-resonance induced spectral emission characteristic of the fluorescent molecules on the plasmon resonant particles.

EXAMPLES

The following specific examples are provided to illustrate features of invention and should not be construed as limiting the scope of the invention as defined by the appended claims.

Example 1

Figure 1A:
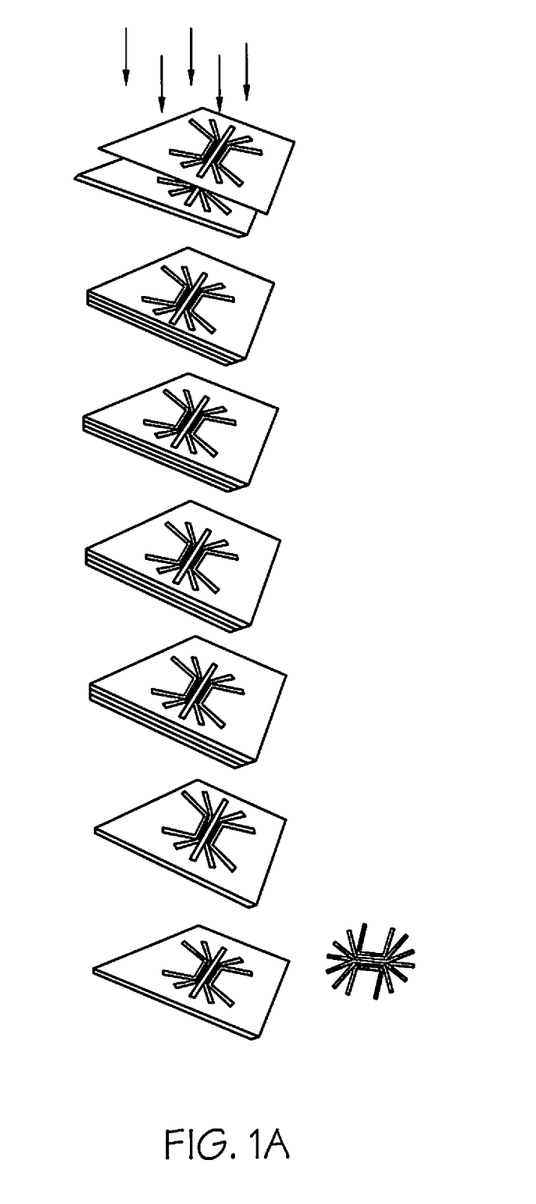
FIG. 1. Is a schematic illustration depicting the steps for fabricating a microfluidic device and a spot plate containing uniform plasmonic nanoparticle arrays.
Figure 1B:
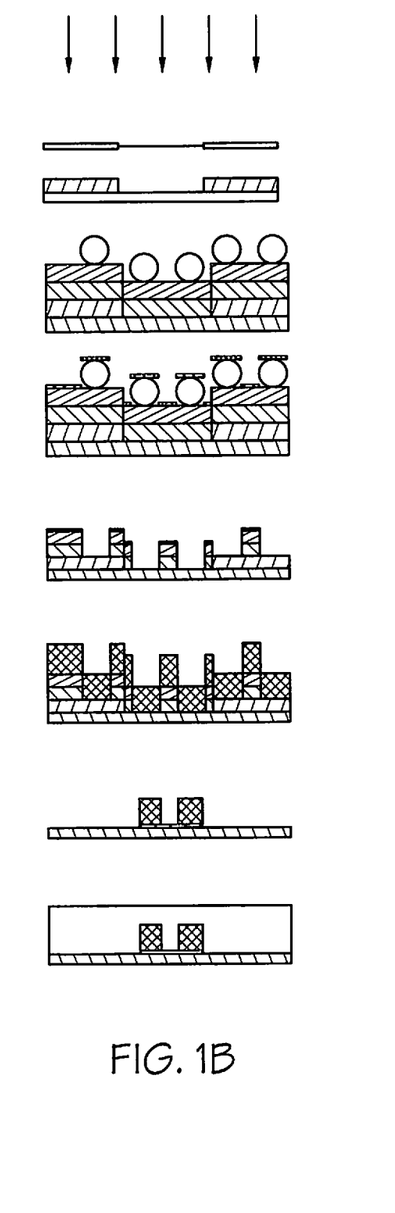
Figure 1C:
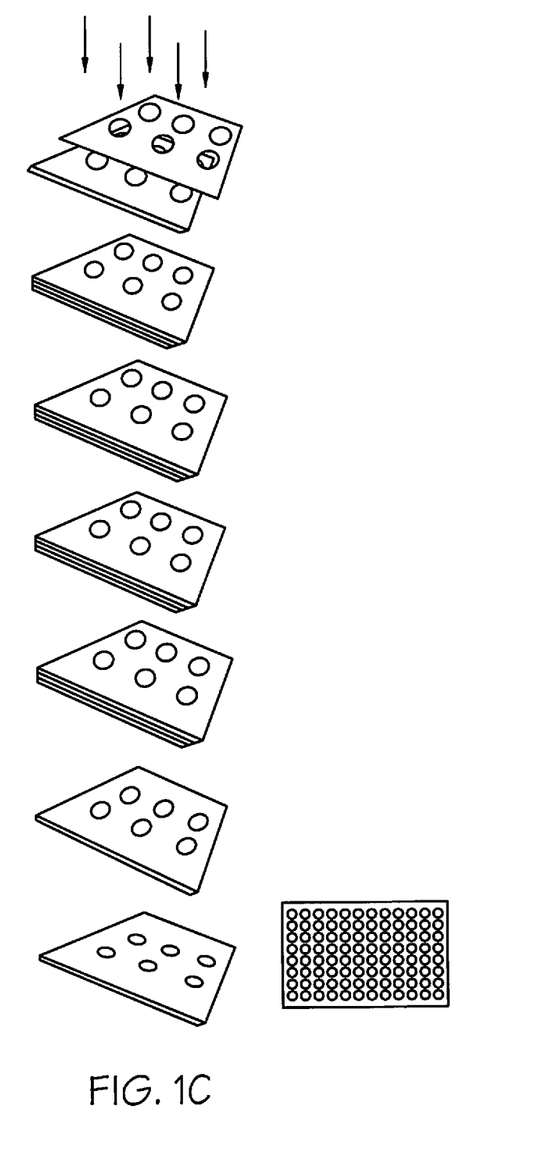

As shown schematically in FIG. 1, a pattern for either microfluidic channels or a spot plate is first made on the substrate using photolithography. Next, the hole mask procedure is carried out on top of the patterned photoresist to make the desired nanoparticle array. Briefly, this procedure involves spin coating a layer of poly(methylmethacrylate) (PMMA) followed by a layer of poly(diallyldimethylammonium chloride) (PDDA). Next, polystyrene spheres of a desired size are drop-coated onto the top of the polymer layers and a layer of 5 nm of gold is deposited over the whole assembly. After removal of the polystyrene spheres by tape-stripping, the masks are subjected to oxygen plasma etching to generate holes the same size as the polystyrene spheres. Metals are then deposited into these holes and in the last step, both the PMMA/PDDA polymer mask and the photoresist are removed using acetone, to create nanoparticle arrays in a desired pattern on the substrate. In this specific example, glass was used as a substrate and the glass substrate was bound to similarly patterned PDMS through oxygen plasma etching, creating a chemical, tight seal in the regions that did not contain nanoparticles. The PDMS layer was used to create the channels for the microfluidic devices and to prevent solution migration from spot to spot in the spot plates. This technique is not only scalable and inexpensive, but also allows for the versatile fabrication of nanoparticle arrays ranging from 20 to 400 nm in diameter in any desirable diffraction-limited pattern. In order to demonstrate the utility of this technique, nanoparticle arrays were patterned to generate both 5 and 7-channel microfluidic devices, as well as a 96-well spot plate that was capable of being measured with a standard plate reader in absorption mode. As would be clear to one of ordinary skill in the art, one could extend the principle to pattern a significantly larger number of microfluidic channels or plates containing 384 or even 1536 spots.

Example 2

Figure 2A:
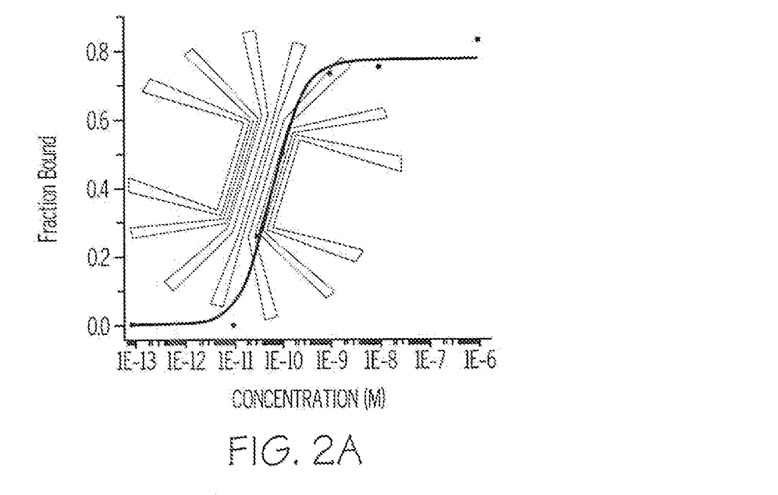
FIG. 2A. A graphical representation of measurement of a one-shot binding curve of Streptavidin binding to biotinylated nanoparticle arrays in the channels of a 7-channel microfluidic device wherein a different concentration of Streptavidin protein was added to each of the 7 channels and allowed to equilibrate for 1 hour, the device was then washed and dried before measuring the change in LSPR peak frequency; 2B) a 5-channel microfluidic device and the corresponding time versus intensity graph for the three channels indicated by the arrows; 2C AFM characterization of a channel in a 5-channel microfluidic device revealing a uniform nanoparticle array that is present only within the channel.
Figure 2B:
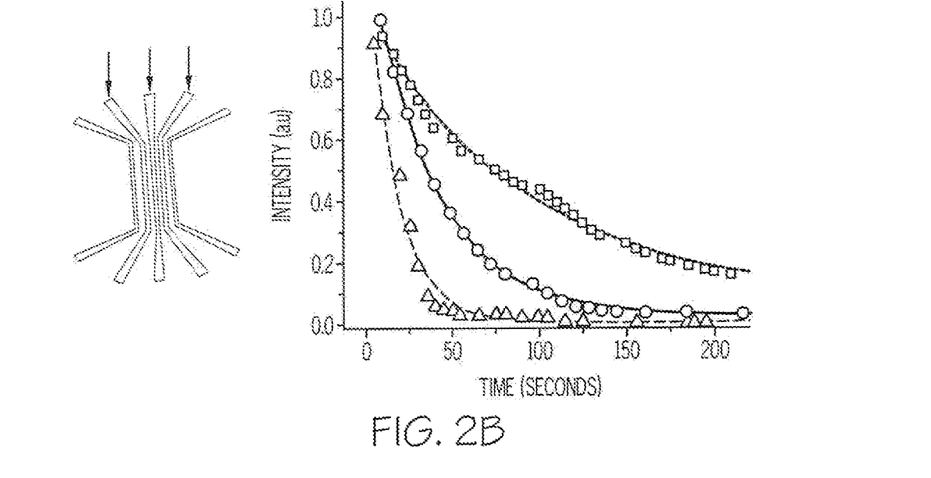
Figure 2C:
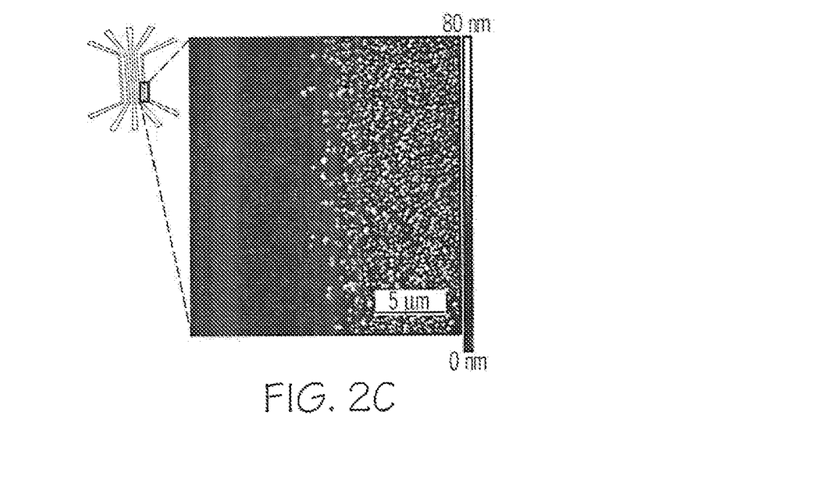

A first proof-of-concept study was carried out with a 7-channel microfluidic device in which different concentrations of Streptavidin protein were added to biotinylated self-assembled monolayers attached to nanoparticle arrays in each channel. Thus, a 7-point binding curve was obtained through the measurement of each channel using a standard UV-Visual spectrometer, see FIG. 2B. The $K_d$ value obtained when fitting the binding curve to a standard Langmuir isotherm, $6\times10^{-11}$ M is in agreement with that observed for Streptavidin binding to nanoparticle arrays generated using nanosphere lithography (Haes, A. J. et al. A nanoscale optical biosensor: Sensitivity and selectivity of an approach based on the localized surface plasmon resonance spectroscopy of triangular silver nanoparticles. *J Am Chem Soc* 2002, 124, 10596-10604, the entire disclosure of which is incorporated herein by this reference). Similarly, a 5-channel microfluidic device was made to study the kinetics of three different concentrations of Streptavidin binding to the same biotinylated nanoparticle arrays. These measurements were carried out by pumping the desired concentration of Streptavidin through a channel using a syringe pump and monitoring a single wavelength with time. The resulting kinetic curves, shown in FIG. 2c, for three different Streptavidin concentrations allow for the calculation of $k_{on}$ and $k_{off}$ rates in a rapid, facile manner.

Figure 3A:
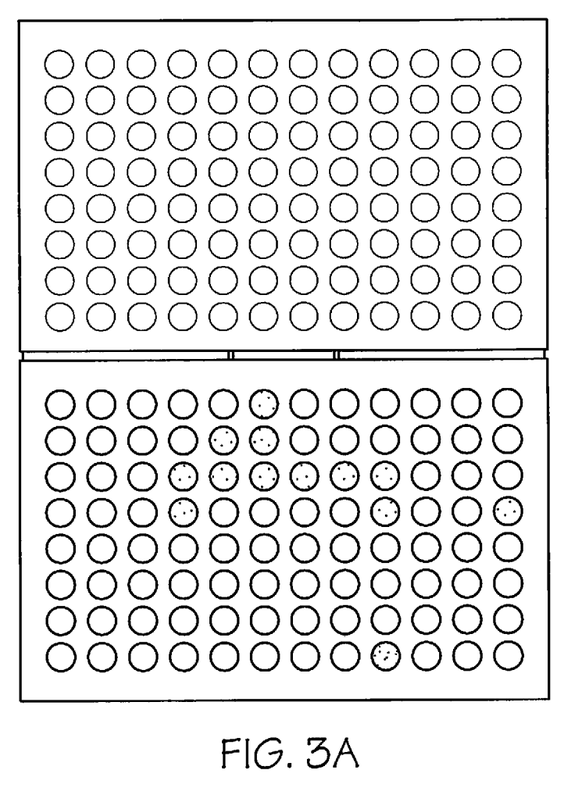
FIG. 3A. A photograph of a 96-well plate containing nanoparticle arrays in each of the 96 wells fabricated according to embodiments of the invention juxtaposed alongside a commercially available 96-well plate; 3B) photograph showing insertion of an inventive well plate into a standard laboratory plate reader.
Figure 3B:
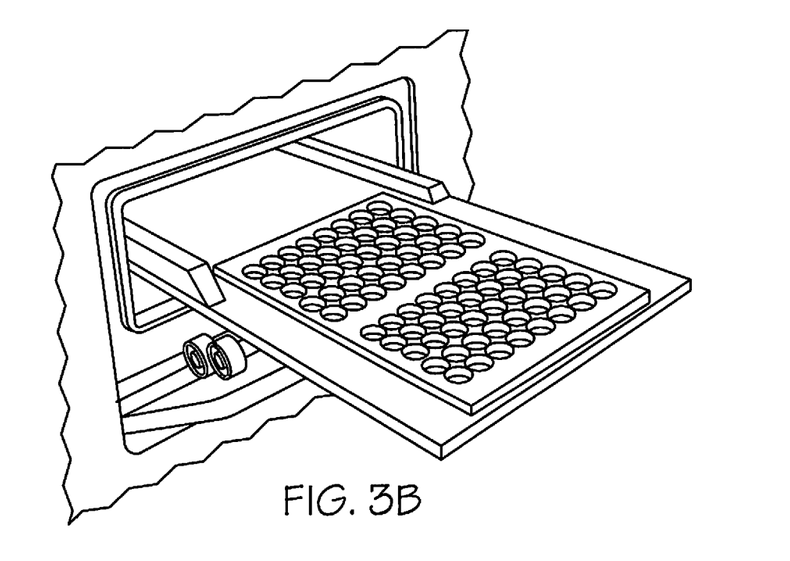

Next, glass/PDMS plates containing 96 spots of nanoparticle arrays were created for multiplexed protein binding measurements, FIG. 3. The surface-bound nanoparticle arrays in each well allowed for facile functionalization and washing of each spot with varying concentrations and protein solutions. Using the 96-spot plate, the binding curves of 6 different protein pairs were simultaneously measured using a standard plate reader; Streptavidin-biotin, Antibiotin-biotin, BSA-antiBSA, TNFα-antiTNFα, MMP-3-antiMMP-3, and Interleukin-10-antiInterleukin-10.

For Streptavidin and Antibiotin binding, thiol-PEG-biotin was added to the nanoparticle arrays. The samples were dried in air and measured both after biotin and protein addition. In order to attract TNF-α, MMP-3, Interleukin-10, and BSA to bind to the nanoparticle arrays, antibodies specific to these proteins were fixed to the nanoparticle arrays by first binding a mixed self-assembled monolayer of octanethiol and mercaptoundecanoic acid. Then, the surface amine groups on the antibodies were coupled using carbodiimide chemistry to the COOH groups of the mercaptoundecanoic acid moieties on the surface. After the self-assembled monolayer or antibodies were coupled to each spot, the plates were dried in air and the LSPR spectra monitored using a plate reader.

Figure 4:
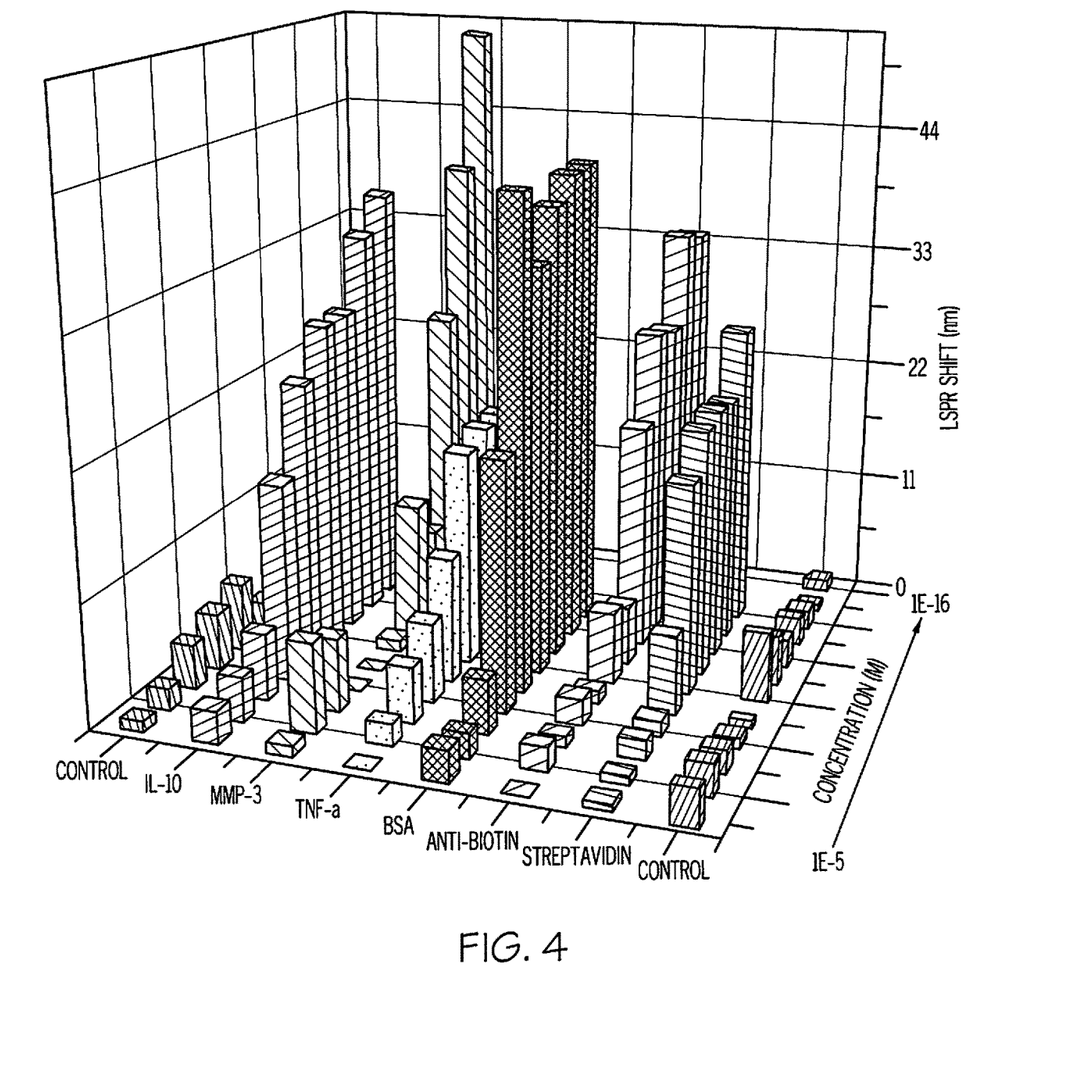
FIG. 4. A 3-dimensional bar graph representation of different binding curves measured simultaneously using the fabricated 96-well plate and a plate reader. The first and last rows in the 96-well plate were used for control experiments in which non-specific binding of the different proteins were measured to either the bare nanoparticle array or a nanoparticle array containing a mixed SAM of OT and MUA. Rows two through six contained different concentrations of Interleukin-10 protein (IL-10), matrix metalloproteinase-3 protein (MMP-3), tumor necrosis factor alpha protein (TNF-α), bovine serum albumin (BSA), Anti-biotin protein, and Streptavidin protein respectively. The data was used to generate six different binding curves with which $K_d$ values could be extracted.
Figure 5A:
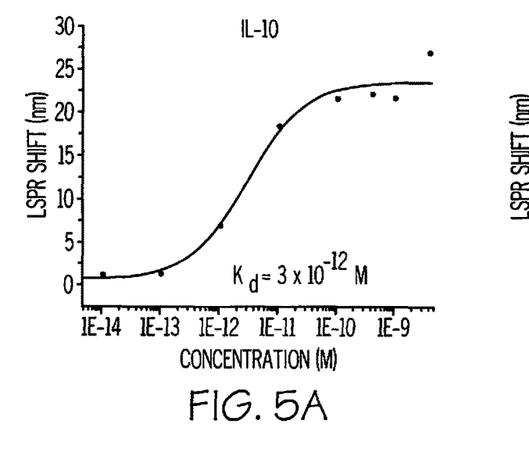
FIG. 5A. Binding curve and extracted $K_d$ value for IL-10; 5B) binding curve and extracted $K_d$ value for Streptavidin; 5C) binding curve and extracted $K_d$ value for MMP-3; 5D) binding curve and extracted $K_d$ value for anti-biotin; 5E) binding curve and extracted $K_d$ value for TNF-α; 5F) binding curve and extracted $K_d$ value for BSA.
Figure 5B:
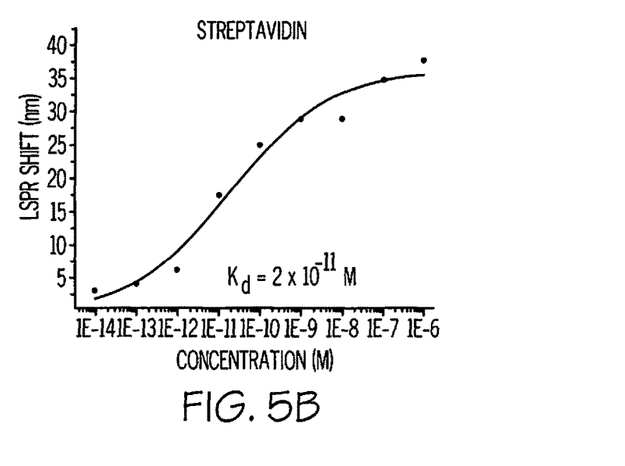
Figure 5C:
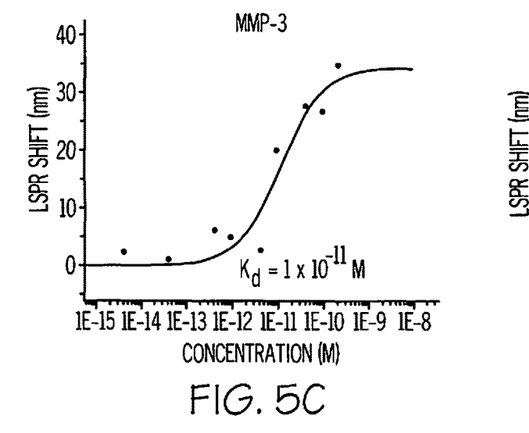
Figure 5D:
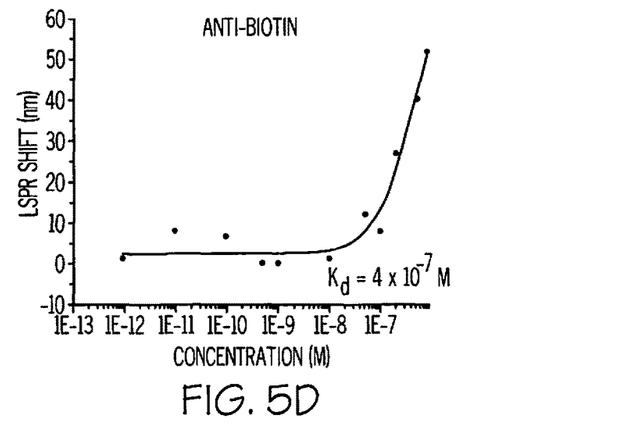
Figure 5E:
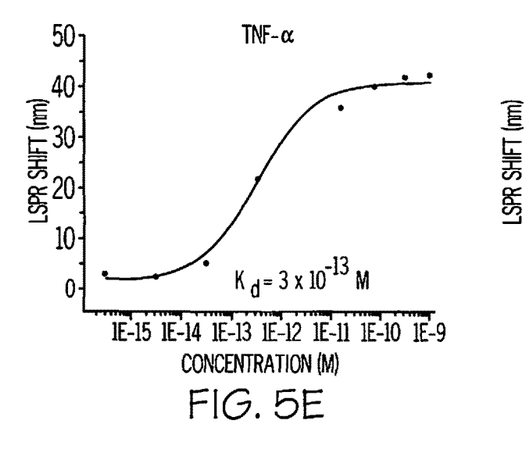
Figure 5F:
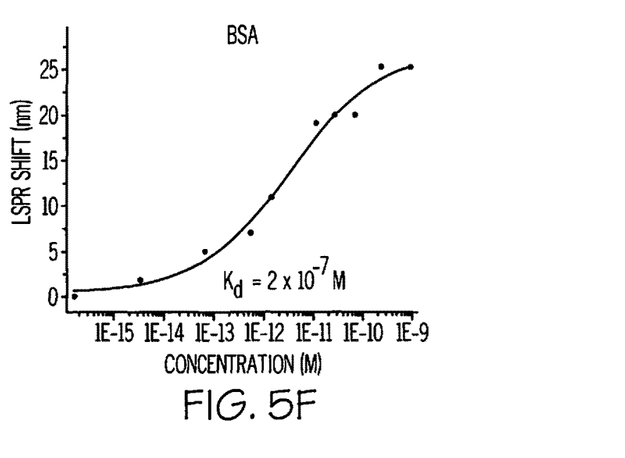
Figure 6:
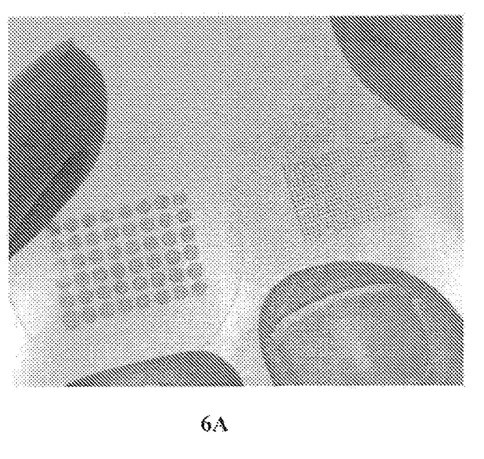

The protein of interest was then added in buffered solution in varying concentration, dried and measured once again in the plate reader to determine the shift in LSPR wavelength accompanying protein binding. As shown in FIG. 4, the two 15-minute measurements with the plate reader were able to produce simultaneous measurements 6 different protein binding curves. The first and last rows of the 96-well plate were taken to run control measurements for non-specific binding of the proteins being tested to the nanoparticle arrays. In row 1, all six proteins were added to the bare nanoparticle arrays and in row 8, the six proteins were added to nanoparticle arrays containing a mixed self-assembled monolayer of octanethiol and mercaptoundecanoic acid. In all cases, the largest LSPR shifts observed for these control measurements were 5-6 nm, significantly lower than the LSPR shifts observed when the appropriate antibody is attached to the nanoparticle arrays. The $K_d$ values shown in FIG. 3b were obtained by fitting the experimental curves to Langmuir binding isotherms and agree nicely with previously published results of these proteins in binding assays utilizing beads, nanoparticles and planar surfaces (see Riboh, J. C. et al. A nanoscale optical biosensor: Real-time immunoassay in physiological buffer enabled by improved nanoparticle adhesion. *J Phys Chem B* 2003, 107, 1772-1780; Hall, W. P. et al. LSPR Biosensor Signal Enhancement Using Nanoparticle-Antibody Conjugates. *J Phys Chem C* 2011, 115, 1410-1414; Wu, P. et al. Toward immobilized antibody microarray optimization: print buffer and storage condition comparisons on performance. *Tech Papers Isa* 2004, 449, 243-248; Reineke, U. et al. Mapping of the interleukin-10/interleukin-10 receptor combining site. *Protein Sci* 1998, 7, 951-960; and Shabani, A. et al. Design of a universal biointerface for sensitive, selective, and multiplex detection of biomarkers using surface plasmon resonance imaging. *Analyst* 2013, 138, 6052-6062, the entire disclosures of which are incorporated herein by this reference).

The inventive methods represent an inexpensive, scalable means to fabricate nanoparticle arrays in any desired pattern on a substrate for multiplexed and/or microfluidic LSPR biosensing measurements. Multiplexed, label-free measurements are increasingly important for a wide range of applications such as point-of-care diagnostics and drug screening. This approach allows for the fabrication of microfluidic devices with significantly more channels than the standard commercially available SPR instrumentation, since the PDMS is chemically sealed to the substrate and can withstand the higher pressures required for smaller channels. Moreover, highly multiplexed spot plates can be fabricated which directly interface with plate readers common to most research laboratories. Lastly, it should be possible to interface these patterned arrays and channels with other on-chip devices for whole cell analysis or gene profiling.

The invention claimed is:
1. A method for fabricating a localized surface plasmon renosance resonance (LSPR) biosensing device comprising a plurality of nanoparticle arrays, the method comprising:
   (a) transferring a desired pattern to a photoresist on a substrate using photolithography;
   (b) spin coating on the photoresist at least a first coat and a second coat of polymer, wherein the polymer of the first coat and the polymer of the second coat are distinct from each other, to form a polymer layer;
   (c) drop coating a plurality of polystyrene particles of a desired shape and size on the polymer layer;
   (d) depositing a nanomeric layer of gold;
   (e) removing the polystyrene particles to create a hole-mask;
   (f) etching the hole mask to generate a plurality of holes;
   (g) depositing a metal into the holes; and

(h) removing the polymer layer and the photoresist to yield a plurality of nanoparticle arrays in a desired pattern.

2. The method according to claim 1, wherein the polymer layer is formed from first spin-coating poly(methylmethacrylate) (PMMA) over the patterned photoresist, followed by spin coating poly(diallyldimethylammonium chloride) (PDDA) over the PMMA to create a polymer layer.

3. The method according to claim 1, wherein the LSPR biosensing device is a microfluidic device, the desired pattern comprises microfluidic channels and the method further comprises (i) providing a poly(dimethylsiloxane) (PDMS) layer comprising a corresponding microfluidic channel pattern, aligning the PDMS layer with the substrate, and sealing the PDMS layer to the substrate in regions of the substrate that do not contain the nanoparticle arrays.

4. The method according to claim 1, wherein the LSPR biosensing device is a spot plate, the desired pattern comprises a spot plate array, and the method further comprises (i) providing a poly(dimethylsiloxane) (PDMS) layer comprising a corresponding spot plate array pattern, aligning the PDMS layer with the substrate, and sealing the PDMS layer to the substrate in regions of the substrate that do not contain the nanoparticle arrays.

5. The method according to claim 1, wherein the substrate is selected from glass, plastic, and paper.

6. The method according to claim 1, wherein the substrate is glass.

7. The method according to claim 5, wherein the substrate is plastic.

8. The method according to claim 7, wherein the plastic comprises nitrocellulose acetate.

9. The method according to claim 1, wherein the nanomeric layer of gold is between 1 and 10 nm thick.

10. The method of claim 9, wherein the nanomeric layer of gold is 5 nm thick.

11. The method according to claim 1 wherein removing the polystyrene particles is effectuated by tape-stripping.

12. The method according to claim 1, wherein etching is effectuated by oxygen plasma etching.

13. The method according to claim 1, wherein the polystyrene particles comprise polystyrene spheres of a same diameter, said diameter between 1 nm and 40 nm.

14. The method according to claim 1, wherein the metal of step (g) is gold or silver.

15. The method according to claim 14, wherein the metal of step (g) is silver and the silver is coated with functionalized silica.

16. The method according to claim 1, wherein one nanoparticle array of the plurality of nanoparticle arrays occupies a circular area having a diameter between about 20 nm and about 400 nm or a non-circular area of between about 320 $nm^2$ and about 12600 $nm^2$.

17. A method for fabricating a localized surface plasmon resonance (LSPR) biosensing device comprising a plurality of nanoparticle arrays, the method comprising:
(a) transferring a desired pattern to a photoresist on a substrate using photolithography, wherein the substrate comprises nitrocellulose acetate;
(b) spin coating at least a first coat and a second coat of polymer, wherein the polymer of the first coat and the polymer of the second coat are distinct from each other, to form a polymer layer;
(c) drop coating a plurality of polystyrene particles of a desired shape and size on the polymer layer;
(d) depositing a nanomeric layer of gold;
(e) removing the polystyrene particles to create a hole-mask;
(f) etching the hole mask to generate a plurality of holes;
(g) depositing a metal into the holes; and
(h) removing the polymer layer and the photoresist to yield a plurality of nanoparticle arrays in a desired pattern.

18. The method according to claim 17, wherein the polymer layer is formed from first spin-coating poly(methylmethacrylate) (PMMA) over the patterned photoresist, followed by spin coating poly(diallyldimethylammonium chloride) (PDDA) over the PMMA to create a polymer layer.

19. The method according to claim 17, wherein the LSPR biosensing device is a microfluidic device, the desired pattern comprises microfluidic channels and the method further comprises (i) providing a poly(dimethylsiloxane) (PDMS) layer comprising a corresponding microfluidic channel pattern, aligning the PDMS layer with the substrate, and sealing the PDMS layer to the substrate in regions of the substrate that do not contain the nanoparticle arrays.

20. The method according to claim 17, wherein the nanomeric layer of gold is between 1 nm and 10 nm thick.

21. The method according to claim 17 wherein removing the polystyrene particles is effectuated by tape-stripping.

22. The method according to claim 17, wherein etching is effectuated by oxygen plasma etching.

* * * * *

UNITED STATES PATENT AND TRADEMARK OFFICE
CERTIFICATE OF CORRECTION

| | |
|---|---|
| PATENT NO. | : 11,280,784 B2 |
| APPLICATION NO. | : 15/932300 |
| DATED | : March 22, 2022 |
| INVENTOR(S) | : Laura Sagle |

It is certified that error appears in the above-identified patent and that said Letters Patent is hereby corrected as shown below:

On the Title Page

Item (56), other publications, cite no. 3, delete "Nano-strucdtured", and insert --Nano-structured--, therefor.

Item (57), Line(s) 2, delete "renosance" and insert --resonance--, therefor.

In the Specification

In Column 2, Line(s) 65, delete "renosance" and insert --resonance--, therefor.

In Column 5, Line(s) 48, delete "renosance" and insert --resonance--, therefor.

In Column 9, Line(s) 26, delete "blosensors" and insert --biosensors--, therefor.

In the Claims

In Column 10, Line(s) 53, Claim 1, delete "renosance".

In Column 11, Line(s) 37, Claim 11, after "claim 1", insert --,--.

In Column 12, Line(s) 43, Claim 21, after "claim 17", insert --,--.

Signed and Sealed this
Thirty-first Day of January, 2023

Katherine Kelly Vidal
*Director of the United States Patent and Trademark Office*